(12) United States Patent
van Laere et al.

(10) Patent No.: US 8,148,350 B2
(45) Date of Patent: Apr. 3, 2012

(54) CARBOHYDRATE COMPOSITION FOR FLAT GLUCOSE RESPONSE

(75) Inventors: Katrien Maria Jozefa van Laere, Heteren (NL); Houkje Bouritius, Zeist (NL); Mirian Lansink, Houten (NL)

(73) Assignee: N.V. Nutricia, Zoetermeer (NL)

( * ) Notice: Subject to any disclaimer, the term of this patent is extended or adjusted under 35 U.S.C. 154(b) by 707 days.

(21) Appl. No.: 12/158,013

(22) PCT Filed: Dec. 20, 2006

(86) PCT No.: PCT/NL2006/050322
§ 371 (c)(1),
(2), (4) Date: Jan. 27, 2009

(87) PCT Pub. No.: WO2007/073187
PCT Pub. Date: Jun. 28, 2007

(65) Prior Publication Data
US 2009/0215718 A1 Aug. 27, 2009

(30) Foreign Application Priority Data

Dec. 20, 2005 (EP) .................................... 05112513

(51) Int. Cl.
*A61K 31/715* (2006.01)
*A61K 47/00* (2006.01)
(52) U.S. Cl. .............. 514/53; 514/54; 514/61; 514/866; 514/909
(58) Field of Classification Search .................... 514/53, 514/54, 61, 866, 909
See application file for complete search history.

(56) References Cited

U.S. PATENT DOCUMENTS

| | | |
|---|---|---|
| 2004/0087514 A1 | 5/2004 | Hughes et al. |
| 2004/0208893 A1 | 10/2004 | Daniels |
| 2005/0203062 A1 | 9/2005 | Levin |

FOREIGN PATENT DOCUMENTS

| | | |
|---|---|---|
| DE | 39 35 906 A1 | 5/1991 |
| DE | 198 29 844 A1 | 1/2000 |
| EP | 1 588 629 A | 10/2005 |
| WO | WO 01/17370 A | 3/2001 |
| WO | WO 2004/084655 A | 10/2004 |

*Primary Examiner* — Shaojia Anna Jiang
*Assistant Examiner* — Everett White
(74) *Attorney, Agent, or Firm* — Gilberto M. Villacorta; Sunit Talapatra; Foley & Lardner LLP

(57) ABSTRACT

A low-glycemic available carbohydrate composition of the invention contains the following components:

(i) 5-60 wt. % of one or more monosaccharides selected from monosaccharides other than glucose and fructose, in particular galactose, ribose and mannose;

(ii) 15-95 wt. % of oligosaccharides having a length of 2 to 20 anhydromonose units, at least half of which are anhydroglucose units linked by non-$\alpha$-1,4 bonds; these oligosaccharides preferably comprising disaccharides such as palatinose, isomaltose and trehalose and/or non-$\alpha$-1,4 linked higher glucose-containing oligosaccharides;

(iii) 0-45 wt. % of other available carbohydrates, such as glucose and maltodextrins.

This carbohydrate composition can be part of a food composition for the treatment of diabetes, obesitas, insulin resistance, or for postprandial glucose response.

18 Claims, No Drawings

CARBOHYDRATE COMPOSITION FOR FLAT GLUCOSE RESPONSE

FIELD OF THE INVENTION

The invention relates to a carbohydrate fraction that gives a sustained and lower glucose release after consumption.

BACKGROUND OF THE INVENTION

Glucose is an important source of energy to the cells in the human body and is abundantly present in food ingredients. After consumption of starch or other dietetic available sources of glucose and their subsequent digestion, glucose is released in the gastro-intestinal tract, where it is rapidly and effectively absorbed from the intestinal lumen. This will usually increase glucose concentrations in blood. The change in glucose after consumption of a food is called the postprandial glucose response (PPGR), which can be measured as the area under the curve (AUC), which plots the plasma glucose concentration with time. The human body strives to maintain homeostasis of glucose levels in tissue and blood with time, in order to allow proper functioning of all cells. One important instrument to achieve glucose homeostasis is the release of insulin by the pancreas when the concentration of specific food components like glucose starts to increase. Under normal circumstances this will increase glucose transport into the cell and the formation of glycogen using glucose, and trigger other metabolic changes, therewith rapidly causing the blood glucose levels to decrease to normal levels.

A person that does not react properly on released insulin is said to be insulin-resistant. Large groups of persons suffer from insulin resistance like many obese persons, persons suffering from the so called metabolic syndrome (or syndrome X), diabetics and many patients in hospitals or nursing homes who developed a temporarily or longer lasting insulin resistance as a cause of their disease. Part of the diabetics also experience an insufficient capacity to increase insulin concentrations in blood after consumption of food (called postprandially). Persons that suffer from insulin-resistance demonstrate abnormal high postprandial glucose response, even after consumption of moderate amounts of food ingredients that comprise glucose. When high postprandial glucose concentrations occur relatively frequently and over longer periods of time, they can cause several severe health problems. Known secondary side effects, as can be found in diabetics, are problems in the cardio-vascular system, such as hypertension, atherosclerosis, bad blood supply to peripheral tissues, stroke, heart attacks etc., as well as problems in the kidney, in particular an abnormal glomerular filtration rate, and a wide range of neuropathies and retinopathies like cataract. It was also found that mortality of severe disease in hospital patients is associated with the severity of insulin resistance.

The decrease of postprandial glucose response (PPGR) has been the subject of numerous research efforts. Many types of carbohydrates have been proposed to induce a low PPGR. Also inclusion of dietetic fibre in parental a nutritional product has been proposed for this purpose, for example viscous fibres, like gums or pectin. The disadvantage of using such fibres is the increase in viscosity, leading to bloating, flatulence, loss of appetite and possibly constipation, when used in liquid products in amounts that are effective.

DE 3935906 discloses the use of galactose for the nutrition of metabolically stressed patients, e.g. suffering from diabetes mellitus. Other saccharides such as glucose, mannose, N-acetylglucosamine, N-acetylgalactosamine, fucose, fructose or lactulose may also be present, although it is preferred that galactose represents at least 50% or even at least 75% of the saccharides. Amino acids, salts etc. are also included in the parenteral administration.

WO03/104473 discloses the galactosylation of hydrogenated and non-hydrogenated isomaltulose to produce oligosaccharides that are useful as probiotics. They are also to be useful for modulating glycemic properties of food products.

WO04/081022 describes a grain composition containing prebiotic isomalto-oligosaccharides obtained by transglucosylation of maltose. The composition can be used for various purposes, including a baking ingredient and an oral rehydration solution.

EP-A 1229803 by Stahl also discloses specific synthetic oligosaccharides obtained by trans-glucosylation, that are slowly digestible.

WO 01/17370 discloses the use of trehalose for providing nutrition to persons suffering from disorders of insulin metabolism. The trehalose replaces other sugars, such as sucrose, glucose and maltose, which should be substantially absent.

It is an object of the invention to provide a nutritional product that is effective in rapidly providing glucose to the consumer and maintaining a clinically significant supply of glucose during a prolonged time without resulting in undesirably high concentrations of glucose in the blood, even in persons that have become insulin-resistant.

It is a further object of the invention to a provide nutritional product for persons that suffer from insulin resistance, in order to prevent development of disorders which result from prolonged and frequent high levels of glucose in blood, such as those diseases that result from advanced glycation products (AGE), neuropathies, retina problems, and kidney problems.

DESCRIPTION OF THE INVENTION

It was found that the combination of one or more of monosaccharides other than glucose and fructose, especially one or more of galactose, mannose and ribose, with glucose-containing oligosaccharides in which the glucose is at least partly linked by non-α-1,4 bonds is suitable as a low glycemic composition which provides glucose to the human body in a slow released and sustained way, wherein the monosaccharides contribute to the glucose availability through metabolic conversion. Not only does this combination have a positive effect on the glycemic and insulinaemic response (GI) or the total area under the PPGR curve, but it also establishes a substantially flat PPGR over longer periods. A desirable PPGR is found to be one that shows a rapid but limited initial increase of the concentration of glucose in blood after administration, in order to give a quick improvement of energy status and prevent too low levels of glucose for proper functioning, and then stabilises for a longer period. This is particularly important for persons suffering from hypoglycemic levels, which are defined to be fasting glucose levels below 3.0 mM.

The low glycemic alpha-gluco-oligosaccharides are characterised as having a GI lower than 60, whereas the above-mentioned non-glucose monosaccharides function as an insulin-releasing agent to stimulate the uptake of the blood glucose, and moreover, to decrease the amount of metabolic stress to the liver. The prolonged increase of plasma glucose levels is especially important for persons that cannot eat at regular intervals and for example as night time formula for infants.

Thus, the invention pertains to a low-glycemic available carbohydrate composition containing a combination of (i) 5-60 wt. % of one or more monosaccharides other than glucose and fructose and (ii) 10-75 wt. % of glucose-containing oligosaccharides having a length of 2 to 20 anhydromonose units, containing at least one non-α-1,4-linked (i.e. non-maltose-type) anhydroglucose unit. It was found that the combination of the monosaccharides, which are insulinotrophic, i.e. stimulate insulin release without substantially increasing blood glucose levels, and the oligosaccharides which also give a low post-prandial glucose response, results in an sustained energy supply with an essential flat glucose response.

As used herein, the term 'low glycemic' means having a glycemic index (GI) below 60, preferably below 50; the GI being commonly understood as being the relative rate of production of blood glucose compared to glucose (having a GI of 100 by definition). The term 'available carbohydrate' is understood to mean a carbohydrate capable of being digested by the enzymes in the gastrointestinal tract. The digestion products or the carbohydrates themselves are absorbed in the first part of the intestine, in particular by the small intestine. Under normal conditions these compounds or their digestion products do not reach the colon. Available carbohydrates can also be defined according to the American Association of Cereal Chemists (AACC) as capable of being absorbed as monosaccharides and metabolised by the (human) body. Food regulations typically oblige manufacturers to mention on the label of a nutritional product inclusion thereof as digestible carbohydrates and they are defined to contribute 4 kcal per g material to the energy content of the product.

The term 'monosaccharides other than glucose and fructose' as used herein comprises any monosaccharide, being an aldose or ketose, or being a pentose or hexose. Examples include ribose, xylose, arabinose, ribulose, galactose, gulose, idose, mannose, sorbose and tagatose. Preferred monosaccharides are ribose, galactose and mannose, and most preferred is galactose. It is preferred that galactose represents at least 25% of the monosaccharides other than glucose and fructose in the composition of the invention. The proportion of such monosaccharides other than glucose and fructose, especially galactose, ribose and/or mannose, in the composition of the invention is preferably 5-45 wt. %, more preferably 8-40 wt. %, most preferably 10-30 wt. % of the available carbohydrates.

Glucose-containing oligosaccharides comprise any and all oligosaccharide having a chain length of 2 up to 20 anhydromonose units containing at least one anhydroglucose unit in any position. The term 'anhydro' is generally used to denote sugar units which are a member of a chain, regardless of their position in the chain and including terminal units. It is preferred that at least half of the anhydromonose units of the oligosaccharides of the carbohydrate composition of the invention are anhydroglucose units. More preferably, the oligosaccharides have a majority of anhydroglucose units, most preferably they contain no more than one anhydromonose unit other than anhydroglucose.

The terms 'anhydroglucose unit linked by non-α-1,4 bonds' or 'non-maltose-linked anhydroglucose unit' are used to denote an anhydroglucose unit (AGU) which is not a terminal or internal α-1,4-linked AGU's. Such an AGU is linked at its anomeric α-position to another anhydromonose unit at another position than the 4-position of a glucose unit or the 2-position of a fructose unit. In particular, such an AGU is linked at its α1-position to the 1-, 3-, 5- or 6-position of another anhydromonose unit or also to the 2-position of another anhydroglucose unit. As a less preferred alternative, or in addition, it may be linked at its 2-, 3- or 6-position with any position of another anhydromonose unit. For example, AGU's may be linked by α-1,1, α-1,2, α-1,3 and α-1,6 bonds. Hence, maltose, sucrose and lactose are not included in these oligosaccharides. One or more α-1,4 linked AGU may be present, as long as differently bound AGU's are also present at least at the same occurrence. Preferably, no more than 1 AGU is linked by an α-1,4 bond.

Examples of such oligosaccharides include the glucosyl-glucose disaccharides isomaltose (α-1,6), nigerose (α-1,3), kojibiose (α-1,2), trehalose (α,α-1,1), gentiobiose (β-1,6), laminaribiose (β-1,3) and sophorose (β-1,2), the hetero-disaccharides primeverose, allolactose, trehalulose, turanose, maltulose, leucrose, isomaltulose (=palatinose), the trisaccharides isomaltotriose, panose, kojitriose, and the like, and the higher homologues up to the decasaccharides, such as isomaltodecaose, and even the icosasaccharides. The disaccharides and trisaccharides are preferred, most preferred are trehalose, trehalulose, palatinose, isomaltose and panose. The glucose-containing oligosaccharides can be obtained from natural sources or synthesised by enzymatic isomerisation of saccharides such as sucrose, and several of them are commercially available. The oligosaccharides can also be obtained by enzymatic transglucosylation of e.g. maltose to produce mainly α-1,6-linked oligoglucoses (isomalto-oligosaccharides). The oligosaccharides may be have a straight chain or may be slightly branched. Further examples include oligonigerose, and alternan-type oligosaccharides.

Not comprised in the available glucose component ii) are so-called resistant malto-dextrins, commercially available as e.g. Fibersol-2 and Nutriose. These have a predominant fibre character, and may partly contain β-linkages. These fibre-type oligosaccharides can be assessed by hydrolysis activity of rat intestinal powder as described by Mishima et al., *J. Agric. Food Chem.* 2005, 53, 7257-7261. Saccharides that are not hydrolysed in this intestinal rat test are considered as not being available.

The preferred proportions of oligosaccharides (ii) in the composition of the invention is 15-75 wt. %, more preferred 18-50 wt. %, of which preferably 10-60 wt. %, more preferably 15-45 wt. %—based on the available carbohydrate composition—consists of disaccharides (ii-a) such as trehalose, trehalulose, palatinose, turanose, leucrose and isomaltose. Among these, the fructose-containing disaccharides, trehalulose, palatinose, turanose and leucrose, and especially palatinose, are of particular interest. Breakdown of palatinose for instance only takes place in the intestines, involving the use of isomaltase.

Preferably, the components (i) and (ii) as defined above together constitute 25-100, preferably 28-75, most preferably 32-60 wt. % of the available carbohydrate composition, and hence the amount of other available carbohydrates (iii) is 0-75, preferably 25-72, most preferably 40-68 wt. %. In an alternative embodiment, the carbohydrate composition according to the invention may contain (iii) 0-45 wt. %, preferably 10-40 wt. % of other available carbohydrates.

Taking into account only components (i) and (ii), which are present in the compositions of the invention in relative proportions of 5-60 and 10-75 weight parts, their proportions on a 100% basis are (i) 5/80-60/70 and (ii) 10/70-75/80, or (i) 6.25-85.7 wt. % and (ii) 14.3-93.75%. The most preferred ratios are (i) 10/60-30/48 (16.7-62.5 wt. % and (ii) 18/48-50/60 (37.5-83.3 wt.). Taking only the disaccharides (ii-a), the relative proportion is (i) 5/65-60/70 (7.7-85.7 wt. %) and (ii-a) 10/70-60/65 (14.3-92.3 wt. %), most preferably (i) 10/55-30/45 (18.2-66.7 wt. %), and (ii-a) 15/45-45/55 (33.3-81.8 wt. %). These ratios apply in particular to the combination of galactose and palatinose. Combinations of these specific monosaccharides and specific disaccharides, for instance galactose and palatinose, exhibit synergism in providing a quick and sustained glucose response.

These other available carbohydrate may first of all comprise (iii-a) available glucose sources, in the form of monomeric glucose or readily available glucose oligomers and polymers such as maltose, maltodextrins, and non-resistant starch; such glucose source contains anhydroglucose units exclusively or predominantly (>90%) bound through α-1,4 linkages. The availability of glucose from these sources can be determined by the method of Englyst et al. (*Am. J. Clin. Nutr.* 1999, 69, 448-454): the proportion of glucose source from which glucose becomes available within 120 minutes from the start of the test is accounted to component (iii) of the composition of the invention. The proportion that does not pass this test is denoted as 'fibre' for the purpose of the invention, and is not accounted for within the present 100% of the available carbohydrate composition as defined herein. Within the available carbohydrates, the proportion of glucose source from which glucose becomes available within 20 minutes from the start of the test is counted as rapidly available glucose sources, according to the Englyst method.

These available glucose sources may be present at such a level that the total glycemic index of the product remains below 75, preferably below 60, especially below 50.

Furthermore, component (iii) may comprise (iii-b) other mono- and di-saccharides. For example, fructose may be present at a level of e.g. 4-25 wt. %, especially 6-18 wt. %, lactose may be present at e.g. from 0 up to about 15 wt. % preferably 1-10 wt. %, sucrose from 0 up to 5 wt. %. The aforementioned amounts of galactose and fructose according to the invention do not comprise the galactose-part of lactose and the fructose-part of sucrose and palatinose when used.

It is preferred that the amount of rapidly available glucose is 1.25-10, more preferably 1.5-6 times the weight amount of free galactose, when galactose is included in the formula. When free ribose is included, the weight amount of rapidly available glucose, in particular of free glucose is 0.8-10 and preferably 1-8 times as high as the amount of free ribose. When free fructose is included, the ratio of the weight of rapidly available glucose to that of fructose is preferably be in the range 1:0-0.12.

It is noted, that for the purpose of defining the composition of the invention, oligosaccharides that are not covered by components (ii) and (iii) are considered not to be available carbohydrates; the same applies to polysaccharides that do not fall under component (iii).

Furthermore, polyols, such as mannitol, lactitol, isomaltitol (isomalt, 6-O-alpha-D-glucopyranosyl-D-sorbitol) etc. are not covered by the components (i), (ii) and (iii), which account for 100% of the available carbohydrate composition. However, such polyols may be present, e.g. at a level of 0-20 wt. % of the available carbohydrate composition.

The available carbohydrate composition may be used as such, e.g. as a supplement, or be part of a partial or complete food product, further containing proteins and/or lipids and/or fibres, minerals, vitamins etc. The composition may be a dry powder, or a solid or semi-solid composition. Preferably, the food product is a liquid, suitable for tube or sip feeding. It has an osmolality of preferably 300-700, more preferably 330-600, most preferably 340-500 mOsm/l, and having an energy density between 0.6 and 2.0, more preferably between 0.75 and 1.5 kcal/ml. In a liquid, the product preferably comprises the available carbohydrate fraction of the invention in an amount of 60-200, preferably 80-160, more preferably 100-140 g/l.

It is advantageous to include non-viscous fibres in the product. Viscous fibres, optionally in combination with other food components, are known to influence gastric emptying rates, and the rate of digestion of foods in the gastrointestinal tract. It is now found that the fibres that preferably are included in the product according the invention should not behave as viscous fibres, neither in the product nor in the gastrointestinal tract. The fibres that can be used according to the invention are advantageously selected in such a way and included in such concentrations that they exhibit a low viscosity in a nutritional composition. Such fibres appear to exhibit a low viscosity also under in vivo conditions. Fibres that can suitably be used are trans galacto-oligosaccharides (GOS), and extensively hydrolysed gums, hydrolysed mannans, hydrolysed arabans, hydrolysed xylans, hydrolysed beta-glucans, hydrolysed fructans (fructose-oligosaccharides, FOS), inulin and/or oligofructoses. Also, so-called resistant (non-digestible) maltodextrin fibres may be used. Such non-viscous, typically soluble fibres are preferably used in an amount of 0-30 wt. %, preferably 4-24 wt. % of the available carbohydrate composition, and thus counting outside the 100% thereof. On energy basis, these fibres can be used at a level of e.g. 0-5 g, especially 0.4-4, in particular 0.6-3 g per 100 kcal, and on a liquid basis, 0-40, preferably 2-30, more preferably 4-25 g/l.

In addition to these non-viscous, soluble fibres, poorly soluble or insoluble fibres such as resistant starch, cellulose and the like may be present, e.g. at a level of 0-30 wt. %, preferably 4-20 wt. % of the available carbohydrate composition, or 0-4, especially 0.3-3 g per 100 kcal, or 0-30, preferably 2-20 g/l.

The total amount of non-starch and resistant starch fibres is preferably in the range of 2-50, preferably 4-40, more preferably 6-30 g/l. The viscosity of the product is low in order to provide acceptable flowing characteristics for sip-drinking and for tube feeding. Measured at 20° C. at a shear rate of 100/sec, viscosity is 1-60, preferably 1.4-40, more preferably 1.8-30 Mpa.s (for reference: the value for water is one).

The nutritional products of the invention may further comprise an insulin-releasing agent, preferably sulfonylurea, and/or an antidiabetic drug, preferably biguanidine and/or thiazolidinedione. If sulfonylurea is present, the composition of the invention preferably contains an amount of 0.1-4 g per kg hereof.

The nutritional compositions of the invention may comprise a protein fraction. Such a protein fraction can be based on a source of vegetable protein, to which at least one free amino acid, a peptide or a protein from animal source can be added. The protein fraction preferably originates for 15-99.9 wt %, preferably 20-95 wt % from plant species belonging to the species of fabales or leguminosae. It is preferred that the proteins originate from one or more members of the group of soybean (*Glycine max*), pea (*Pisum* species), bean (*Phaseolus* species), fenugreek (*Trigonella* species), lupin, lentil (*Lens* species), peanut (*Arachis* species), tamarind, clover and alfalfa. Such protein compositions further support the improvement of postprandial glucose response and postprandial insulin response. The amino acids or peptides are selected to be rich in those amino acids which increase nutritional value of the protein fraction as a whole in terms of the demand for essential amino acids. In particular these amino acids are lysine, leucine and phenylalanine. The compositions may comprise per 100 g amino acids 1.8-5 g methionine, and/or 4.5-9 g threonine, and/or 8.6-17 g leucine, and/or 5.5-9.5 g proline. The protein source of animal origin is selected in particular from milk proteins and liquefied proteins from muscle from animal or fish-like hydrolysed proteins. Milk proteins are particularly preferred, especially whey proteins and more in particular those whey proteins that comprise less than 40 wt % and preferably less than 30 wt. % kappa-casein or glycomacropeptide, calculated on protein base.

The amount of protein in the products is preferably 0.5-15 g, more preferably 1-10 and most preferably 2-7 g per 100 ml product. Calculated as the amount of energy that is provided by proteins, lipids and digestible carbohydrates, by using the Atwater factors (4, 9, 4, respectively) for each of them, the amount of energy for protein is 10-30, preferably 14-28, most preferably 17-26 en %, and for digestible carbohydrates 35-70, preferably 40-60 and most preferably 42-55 en %. The composition comprises 5-80, preferably 20-50 g/l of a protein fraction.

The nutritional compositions of the invention can further comprise a fat or lipid fraction. Such a lipid fraction comprises oleic acid and essential fatty acids like linoleic acid and alpha-linolenic acid, but could also comprise conjugated linolenic acids and omega-3 long chain fatty acids like eicosapentaenoic acid and docosahexaenoic acid. The fatty acids preferably comprise less than 10 wt % saturated fatty acids, and less than 1 wt % of trans fatty acids. The amount of lipid is 10-60, preferably 15-50, more preferably 31-46 g/l. Expressing the amount of lipid in the product as en % using the Atwater factors the amount of lipid is 25-45, preferably 28-40 and most preferably 30-38 en %. Lipids include triglycerides, diglycerides, monoglycerides, (lyso)phospholipids, sphingolipids and ceramides. Other components that are soluble in petroleum ether or hexane, like cholesterol and other sterols, are not included in calculations about the lipid fraction.

Moreover the product can comprise micro-ingredients like vitamins, trace elements and minerals that are known in the art and carnitine equivalents, inositol, taurine and other food constituents such as flavours, colorants or manufacturing aids. The amount of calcium and phosphorous are also selected to be within the range of 10-70, preferably 20-60 mg/100 ml. The ratio of calcium to phosphorous is in the range 0.8-2, preferably 1.1-1.9, more preferably 1.3-1.8.

The available carbohydrate composition and nutritional composition according to the invention are useful in maintaining a low and prolonged glucose response in blood and tissue after consumption, and especially useful in cases of diabetics and/or insulin-resistance. People that suffer from or are extremely susceptible to insulin-resistance are e.g. severely or critically ill patients, in particular palliative patients like those that suffer from severe cancer or HIV infection. Other groups of patients suffering from difficulties to control their PPGR comprise those persons that were subjected to major surgery or exposed to other traumata, malnourished persons in particular those suffering from protein-energy malnutrition, persons that suffer from obesity, the Metabolic Syndrome, Syndrome X, hyperglycaemia, hyperinsulinaemia, dyslipidaemia, hypertriglyceridaemia and dysfibrinolysis, but also large parts of the group of the elderly in Western societies. In addition the product can be useful for persons that have an increased risk in terms of a hereditary history of developing insulin resistance, PPGR in the mammal's blood for a period starting after 20 minutes to 4 hours after administration. It is even more preferred to maintain the glucose concentration stable until 3 hours, more preferably until 2 hours after administration. A substantially flat glucose level or PPGR means that the glucose level in blood does not vary more than about 1.6 mM and preferably less than 1.3, more preferably less than 1.0 mM per 20 minutes during the above-mentioned period after consumption.

In case of diabetics, the glucose blood levels are typically maintained between 4 mM and 15 mM. However, in the case of severe diabetics, peak postprandial glucose concentrations above 15 mM can still be observed. Under these circumstances the nutritional composition comprising the carbohydrate fraction of the invention should be consumed in more than one eating session and/or in combination with administration of an appropriate amount of insulin prior to consumption of the food product. In case of non-diabetics it is possible to control the glucose blood level even below 11 mM.

Preferably the glucose levels in plasma can be controlled between 5 and 8 mM in the abovementioned period, without the necessity to consume large amounts of fibre with it, as this may cause gastrointestinal discomfort, and without replacing glucose sources by other carbohydrates, which demand an unrealistic high metabolic capacity in the person, or by high amounts of lipids, which may disturb obesity or diabetics like many Hindustan persons and several Caucasian families, for persons that plan irregular feeding pattern, like sportsmen during an enduring exercise or persons that desire to maintain attention for longer periods of time, like students during studying or examines or during meetings.

Thus, the available carbohydrate compositions and nutritional compositions of the invention can be used for the prevention and/or treatment of diabetics, insulin-resistance, obesity, controlling postprandial glucose response, metabolic syndrome, syndrome X, hyperglycaemia, hyperinsulinaemia, dyslipidaemia, hypertriglyceridaemia, dysfibrinolysis and/or disorders associated with major surgery or trauma in a mammal, by maintaining a substantially stable glucose level or physiologically acceptable blood lipid or cholesterol profiles.

Moreover the products are effective in decreasing the risk for obtaining and decreasing the aggravation of several diseases which are associated with frequently elevated blood glucose levels, which include retinopathies, kidney diseases and neuropathies. Also diseases associated with the occurrence of advanced glycation products (AGE) can be prevented. Effectiveness of the product can be determined by measuring the levels of glycated haemoglobin molecules (Hb1Ac) in blood.

EXAMPLE 1

Two liquid formulas A and B for diabetes patients were prepared containing the following ingredients per 100 ml:

|  | A | B |
|---|---|---|
| Total protein | 4.75 (19 en %) | 4.75 (19 en %) |
| Total lipids | 3.78 (34 en %) | 3.78 (34 en %) |
| Total available carbohydrates | 11.15 (47 en %) | 11.75 (47 en %) |
| Galactose | 1.5 | 1.75 |
| Ribose | 0.3 | — |
| Palatinose | 3.0 | 2.0 |
| Isomaltitol | 0.6 | — |
| Isomalto-oligosaccharides | — | 2.75 |
| Glucose | 1.5 | 1.7 |
| Maltodextrins | 3.0 | 2.2 |
| Non-resistant starch # | 1.0 | 0.9 |
| Lactose * | 0.6 | 0.25 |
| Fructose | 0.15 | 0.2 |
| Total fibres | 2.0 | 2.0 |
| Galacto-oligosaccharides (GOS) | 0.9 | — |
| Hydrolysed guar | — | 1.0 |
| Cellulose | 0.1 | 0.1 |
| Resistant starch ## | 1.0 | 0.9 |
| Vitamins, minerals, water | + | + |

The digestible (available) part of a commercial resistant starch ingredient
The non-digestible part of a commercial resistant starch ingredient
* Including the lactose of the GOS ingredient

EXAMPLE 2

Liquid compositions C and D (sipfeed or tubefeed) for diabetes patients were prepared containing the following ingredients per 100 ml:

| | | |
|---|---|---|
| Energy: | 419 kJ | |
| | (100 kcal) | |
| Protein fraction: | 19.4 en % | 4.86 g |
| α-Lactalbumin-enriched whey protein | | 2.43 g |
| Soy protein | | 2.43 g |
| Lipid fraction: | 34.2 en % | 3.80 g |
| rapeseed/sunflower (Canola HO blend 331) | | 3.17 g |
| sunflower oil HOA (Trisun 347) | | 0.20 g |
| low-erucic rapeseed oil (Canola 338) | | 0.20 g |
| marinol | | 0.10 g |
| other | | 0.13 g |
| Digestible carbohydrate fraction: (see below) | 46.4 en % | 11.63 g |
| Fibre: | | 2.00 g |
| galacto-oligosaccharides | | 1.00 g |
| cellulose | | 0.10 g |
| Nutrilose FM06 (non-digestible part) | | 0.65 g |
| resistant starch (non-digestible part) | | 0.25 g |
| Minerals: (in mg) | | |

Na (37.5), K (100), Cl (37.5), Ca (47.0), P (37.5), Mg (23.0)
Trace elements: (in µg)

Fe (1600), Zn (1400), Cu (210), Mn (330), F (100),
Mo (10.0), Se (7.5), Cr (12.0), I (13.0)
Vitamins: (in µg)

vit. A (82 RE), carotenoids (200), vit. D (1.2), vit. E (2500 α-TE),
vit. K (5.3),vit. B1 (400), vit. B2 (200), niacin (1800 NE), pantothenic acid (800), vit. B6 (300), folic acid (38), vit. B12 (0.65), biotin (6.5),
vit. C (15.0), choline (37).

Compositions C and D differ in the digestible carbohydrate fraction, as follows:

| | C | D |
|---|---|---|
| Total available carbohydrates | 11.63 | 11.63 |
| Galactose | 1.50 | 1.50 |
| Fructose | 1.50 | — |
| Palatinose | 2.40 | 4.40 |
| Alternan, DP 10 | 2.00 | — |
| Glucose | 1.50 | 1.50 |
| Cleargum (tapioca starch) | 0.80 | 2.80 |
| Digestible part of resistant starch product | 0.25 | 0.25 |
| Digestible part of Nutriose FM06 | 0.12 | 0.12 |
| Other * | 1.56 | 1.06 |

* Including the lactose of the GOS ingredient

The invention claimed is:

1. A low-glycemic carbohydrate composition comprising the following components:
   (i) 5-60 wt. % of one or more monosaccharides, wherein the monosaccharides are not glucose or fructose;
   (ii) 10-75 wt. % of oligosaccharides having a length of 2 to 20 anhydromonose units, wherein the oligosaccharides are selected from the group consisting of trehalose, trehalulose, palatinose, isomaltose, turanose and leucrose;
   (iii) 0-75 wt. % of other available carbohydrates.

2. The carbohydrate composition according to claim 1, wherein components (i) and (ii) constitute 28-75 wt. % of the composition.
3. The carbohydrate composition according to claim 2, wherein components (i) and (ii) constitute 32-60 wt. % of the composition.
4. The carbohydrate composition according to claim 1 or 2, comprising: (i) 8-40 wt. % of one or more monosaccharides selected from galactose, ribose and mannose.
5. The carbohydrate composition according to claim 1, wherein the monosaccharides of component (i) are selected from the group consisting of ribose, xylose, arabinose, ribulose, galactose, gulose, idose, mannose, sorbose and tagatose.
6. The carbohydrate composition according to claim 1, comprising: (ii) 10-50 wt. % of the oligosaccharides.
7. The carbohydrate composition according to claim 6, wherein the oligosaccharides are selected from the group consisting of trehalose, trehalulose, palatinose and isomaltose.
8. The carbohydrate composition according to claim 6, comprising: (ii) 18-45 wt. % of the oligosaccharides.
9. The carbohydrate composition according to claim 1, further comprising 2-30 wt. %, based on the total dry weight of components i)-iii) in the composition, of nutritional fibres.
10. The carbohydrate composition according to claim 1, comprising (i) 5-60 wt. % of galactose and (ii) 10-60 wt. % of palatinose.
11. The carbohydrate composition according to claim 10, comprising (i) 10-30 wt. % of galactose and (ii) 15-45 wt. % of palatinose.
12. The carbohydrate composition according to claim 1, wherein the monosaccharides comprise galactose, ribose, mannose, or a combination thereof.
13. The carbohydrate composition according to claim 1, comprising: (i) 8-40 wt. % of one or more monosaccharides selected from galactose, ribose and mannose.
14. The carbohydrate composition according to claim 13, comprising: (i) 10-30 wt. % of one or more monosaccharides selected from galactose, ribose and mannose.
15. The carbohydrate composition according to claim 13, comprising: (i) 8-40 wt. % of galactose.
16. The carbohydrate composition according to claim 1, comprising: (ii) 10-60 wt. % of oligosaccharides selected from the group consisting of trehalose, palatinose, turanose and leucrose.
17. A method for the treatment of diabetes, obesity, insulin resistance, or for postprandial glucose response in a patient, comprising administering to the patient the carbohydrate composition according to claim 1.
18. A liquid nutritional composition comprising:
   (i) 5-60 wt. % of one or more monosaccharides, wherein the monosaccharides are not glucose or fructose;
   (ii) 10-75 wt. % of oligosaccharides having a length of 2 to 20 anhydromonose units, wherein the oligosaccharides are selected from the group consisting of trehalose, trehalulose, palatinose, isomaltose, turanose and leucrose;
   (iii) 0-75 wt. % of other available carbohydrates; and
   (iv) lipids and/or proteins, the available carbohydrates accounting for 35-70 en % of the nutritional composition.

* * * * *